United States Patent
Lewis et al.

(10) Patent No.: US 8,882,498 B2
(45) Date of Patent: Nov. 11, 2014

(54) COORDINATED METAL AND CERAMIC ORTHODONTIC BRACKET SYSTEMS

(75) Inventors: Paul E. Lewis, Midvale, UT (US); Dwight P. Schnaitter, Salt Lake City, UT (US)

(73) Assignee: Ultradent Products, Inc., South Jordan, UT (US)

(*) Notice: Subject to any disclaimer, the term of this patent is extended or adjusted under 35 U.S.C. 154(b) by 271 days.

(21) Appl. No.: 13/255,489

(22) PCT Filed: Mar. 15, 2010

(86) PCT No.: PCT/US2010/027296
§ 371 (c)(1),
(2), (4) Date: Nov. 29, 2011

(87) PCT Pub. No.: WO2010/114691
PCT Pub. Date: Oct. 7, 2010

(65) Prior Publication Data
US 2012/0094247 A1    Apr. 19, 2012

Related U.S. Application Data

(60) Provisional application No. 61/166,557, filed on Apr. 3, 2009.

(51) Int. Cl.
*A61C 3/00* (2006.01)
*A61C 7/14* (2006.01)

(52) U.S. Cl.
CPC ........................................ *A61C 7/14* (2013.01)
USPC ............................................................. 433/9

(58) Field of Classification Search
USPC ...................................................... 433/9–17
See application file for complete search history.

(56) References Cited

U.S. PATENT DOCUMENTS

| | | | |
|---|---|---|---|
| 479,882 A | * | 8/1892 | Kesling ........................ 209/273 |
| 4,355,975 A | | 10/1982 | Fujita |
| 4,687,441 A | | 8/1987 | Klepacki |
| 4,799,882 A | | 1/1989 | Kesling |
| 4,915,625 A | | 4/1990 | Tsukuma et al. |
| 4,978,391 A | | 12/1990 | Jones |

(Continued)

FOREIGN PATENT DOCUMENTS

| | | |
|---|---|---|
| DE | 20314121 | 12/2003 |
| DE | 2005013890 | 11/2005 |
| WO | WO 00/33760 | 6/2000 |
| WO | 2004004592 | 1/2004 |

OTHER PUBLICATIONS

U.S. Appl. No. 11/613,767, Dec. 17, 2012, Office Action.

(Continued)

*Primary Examiner* — Sunil K Singh
(74) *Attorney, Agent, or Firm* — Workman Nydegger

(57) ABSTRACT

Coordinated metal and ceramic orthodontic bracket systems (100) allow a practitioner to insert one or more ceramic brackets (102, 104, 106, 108) into a metal bracket system (1001), replacing selected metal brackets (102', 1041, 106', 108') with ceramic brackets (102, 104, 106, 108), and vice-versa. Thus, both a ceramic bracket system (100) and a metal bracket system (1001) are provided, in which corresponding brackets of each system include substantially identical "in-out" slot floor cross-sectional thicknesses so that corresponding brackets are interchangeable with each other, without any need for compensating bends or later treatment to correct unintended buccal-lingual tooth movement.

18 Claims, 4 Drawing Sheets

(56) References Cited

U.S. PATENT DOCUMENTS

| | | | |
|---|---|---|---|
| 5,032,080 | A | 7/1991 | Hakansson et al. |
| 5,096,417 | A | 3/1992 | Greenberg |
| 5,116,885 | A | 5/1992 | Hattori |
| 5,356,288 | A | 10/1994 | Cohen |
| 5,607,299 | A | 3/1997 | Nicholson et al. |
| 5,716,208 | A | 2/1998 | Forman |
| 5,762,492 | A | 6/1998 | Kanomi et al. |
| 5,857,849 | A | 1/1999 | Kurz |
| 6,071,118 | A | 6/2000 | Damon |
| 6,142,775 | A | 11/2000 | Hansen et al. |
| 6,267,590 | B1 | 7/2001 | Barry et al. |
| 6,350,792 | B1 | 2/2002 | Smetana |
| 6,506,049 | B2 | 1/2003 | Hanson |
| 6,607,383 | B2 | 8/2003 | Abels et al. |
| 6,616,445 | B2 | 9/2003 | Abels et al. |
| 6,663,385 | B2 | 12/2003 | Tepper |
| 6,960,081 | B2 | 11/2005 | Abels |
| 7,125,249 | B1 | 10/2006 | Lauren |
| 7,134,872 | B2 | 11/2006 | Abels |
| 7,204,691 | B2 | 4/2007 | Darling et al. |
| 7,611,352 | B2 | 11/2009 | Abels |
| 2002/0110771 | A1 | 8/2002 | Abels et al. |
| 2002/0110772 | A1 | 8/2002 | Abels et al. |
| 2002/0110773 | A1 | 8/2002 | Abels et al. |
| 2002/0110774 | A1 | 8/2002 | Abels et al. |
| 2002/0110775 | A1 | 8/2002 | Abels et al. |
| 2002/0110777 | A1 | 8/2002 | Abels et al. |
| 2002/0110778 | A1 | 8/2002 | Abels et al. |
| 2002/0119414 | A1 | 8/2002 | Orikasa |
| 2002/0187452 | A1 | 12/2002 | Abels et al. |
| 2003/0008259 | A1 | 1/2003 | Kuo et al. |
| 2003/0022124 | A1* | 1/2003 | Schnaitter et al. ............. 433/19 |
| 2003/0165790 | A1* | 9/2003 | Castro et al. ..................... 433/8 |
| 2004/0086824 | A1* | 5/2004 | Kesling .............................. 433/9 |
| 2004/0152034 | A1 | 8/2004 | Cummings et al. |
| 2004/0157186 | A1 | 8/2004 | Abels et al. |
| 2005/0186525 | A1 | 8/2005 | Abels et al. |
| 2005/0196729 | A1 | 9/2005 | Jessop et al. |
| 2005/0244776 | A1 | 11/2005 | Abels et al. |
| 2005/0255422 | A1 | 11/2005 | Cordato |
| 2005/0266268 | A1 | 12/2005 | Tsuboyama |
| 2006/0003281 | A1 | 1/2006 | Nicholson |
| 2006/0210942 | A1 | 9/2006 | Pace et al. |
| 2006/0228664 | A1* | 10/2006 | Castner et al. .................. 433/11 |
| 2007/0099145 | A1 | 5/2007 | Abels |
| 2007/0134612 | A1* | 6/2007 | Contencin ...................... 433/24 |
| 2008/0057459 | A1* | 3/2008 | Abels et al. .................... 433/10 |

OTHER PUBLICATIONS

Ramakrishna, Seeram, "An Introduction to Biocomposites", Imperial College Press (Jun. 2004) pp. 180-191.

"3M Self Litigating Braces—Frequently Asked Questions" (2006) http://soultions.3m.com/wps/portal/3M/en_US/Clarity/braces/product-info/questions/. Available at least as early as Feb. 26, 2009.

Alliance Dental & Orthodontics, http://www.alliancedentalandorthodontics.com/types.asp. Available at least as early as Feb. 26, 2009.

"Braces Review", http://www.bracesreview.com/forums/new-member-introductions/2540-too-many-options-ceramic-vs-damon-vs-aoos-damons.html, Dec. 6, 2008.

"Clear Braces", Mountain View Orthodontist. (2006) http://www.drashouri.com/clear-braces.html. Available at least as early as Feb. 26, 2009.

"Online Guide to Braces" (@007) http://www.bracesguide.com/bracesbasic/bracesbasics2.html. Available at least as early as Feb. 26, 2009.

U.S. Appl. No. 10/932,634, Apr. 6, 2006, Office Action.
U.S. Appl. No. 10/932,634, Aug. 24, 2006, Notice of Allowance.
U.S. Appl. No. 11/469,157, Oct. 17, 2007, Office Action.
U.S. Appl. No. 11/469,157, Apr. 14, 2008, Office Action.
U.S. Appl. No. 11/469,157, Aug. 11, 2008, Office Action.
U.S. Appl. No. 11/469,157, Oct. 20, 2008, Office Action.
U.S. Appl. No. 11/469,157, Feb. 3, 2009, Office Action.
U.S. Appl. No. 11/469,157, Aug. 13, 2009, Notice of Allowance.
U.S. Appl. No. 11/613,767, Sep. 3, 2008, Office Action.
U.S. Appl. No. 11/613,767, Dec. 16, 2008, Office Action.
U.S. Appl. No. 11/613,767, Jun. 4, 2009, Office Action.
U.S. Appl. No. 11/613,767, Dec. 30, 2009, Office Action.

* cited by examiner

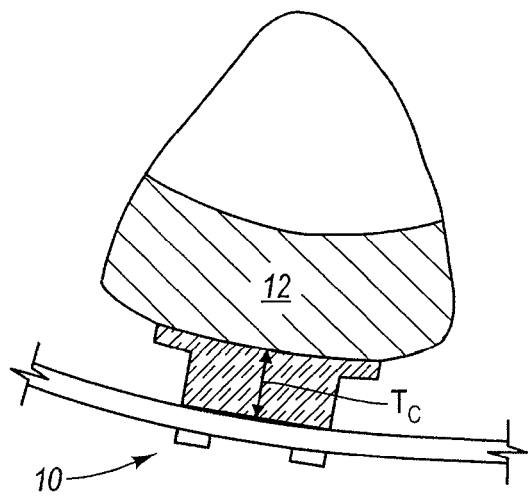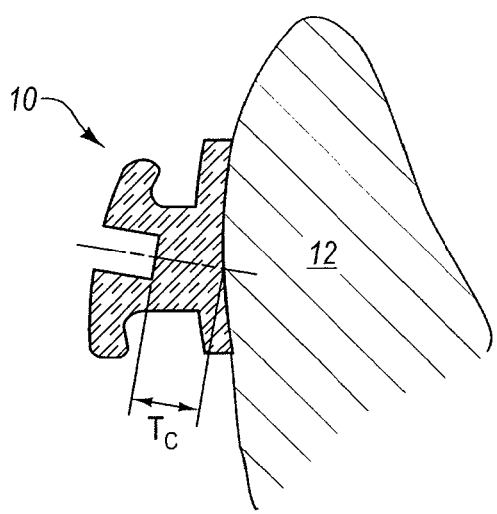
Fig. 1A  Fig. 1B
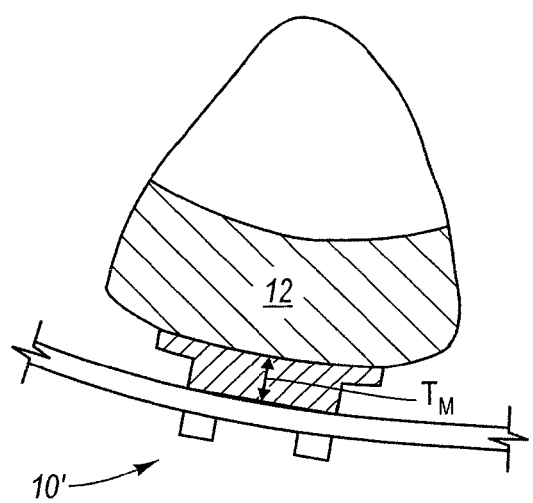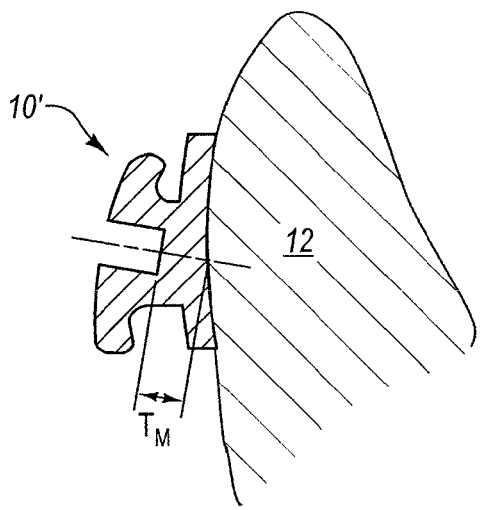
Fig. 2A  Fig. 2B

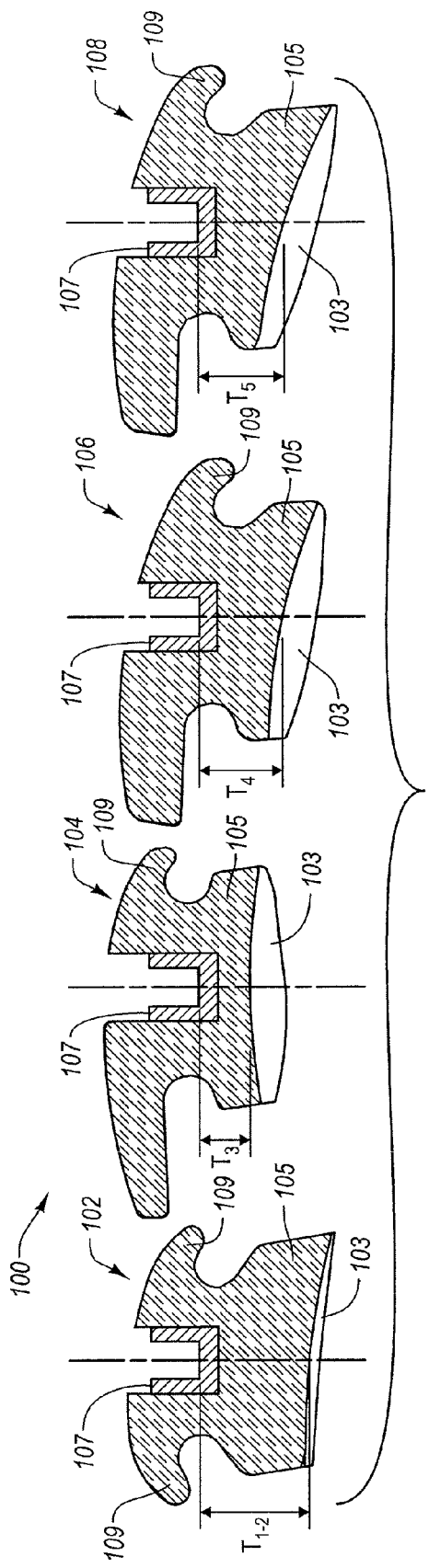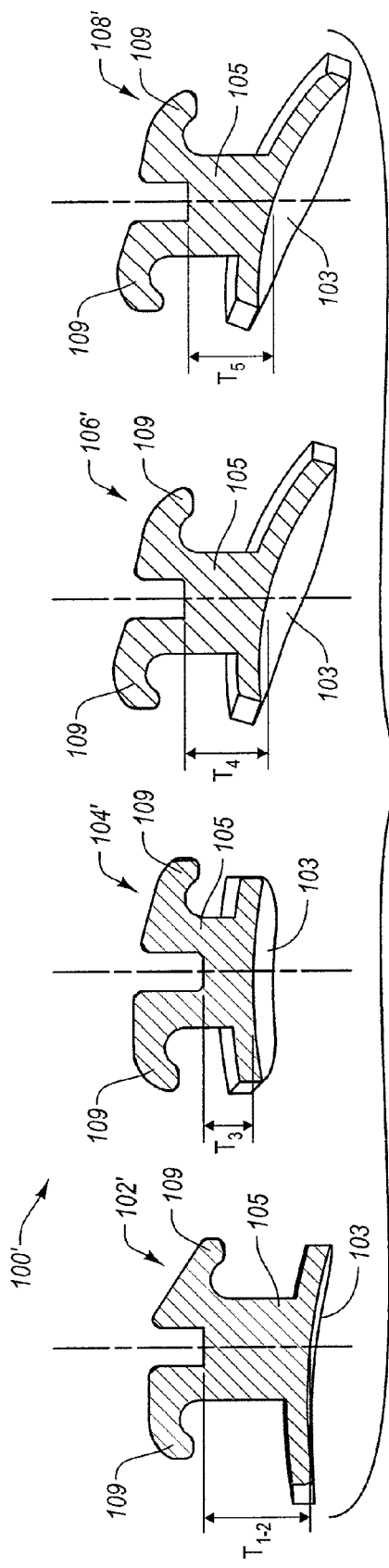
Fig. 3A
Fig. 3B

COORDINATED METAL AND CERAMIC ORTHODONTIC BRACKET SYSTEMS

CROSS-REFERENCE TO RELATED APPLICATIONS

This Patent Application is a U.S. National Stage of International Application No. PCT/US2010/027296, filed on Mar. 15, 2010, which claims priority to US Provisional Application No. 61/166,557 filed on Apr. 3, 2009, the disclosures of which are incorporated herein by reference in their entireties.

BACKGROUND OF THE INVENTION

1. The Field of the Invention

The present invention relates to orthodontic bracket systems.

2. The Relevant Technology

Orthodontics is a specialized field of dentistry that involves the application of mechanical forces to urge poorly positioned or crooked teeth into correct alignment and orientation. Orthodontic procedures can be used for cosmetic enhancement of teeth, as well as medically necessary movement of teeth to correct underbites or overbites. For example, orthodontic treatment can improve the patient's occlusion and/or enhanced spatial matching of corresponding teeth.

The most common form of orthodontic treatment involves the use of orthodontic brackets and wires, which together are commonly referred to as "braces." Orthodontic brackets are small slotted bodies configured for direct attachment to the patient's teeth or, alternatively, for attachment to bands which are, in turn, cemented or otherwise secured around the teeth. Once the brackets are affixed to the patient's teeth, such as by means of glue or cement, a curved arch wire is inserted into the bracket slots. The arch wire acts as a template or track to guide movement of the teeth into proper alignment. End sections of the arch wire are typically captured within tiny appliances known as tube brackets or terminal brackets, which are affixed to the patient's bicuspids and/or molars. The remaining brackets typically include open arch wire slots and apply orthodontic forces by means of ligatures attached to the brackets and arch wire (e.g., by means of tie wings on the brackets).

Orthodontic bracket systems are typically either made of metal, ceramic, or plastic. Plastic brackets are less preferred because they tend to stain easily, and are not as strong as the alternative materials. Ceramic brackets are often preferred by patients over metal brackets because they can be formed so as to be transparent or translucent, although they are significantly more expensive. Because of the greater expense associated with ceramic brackets, as a compromise between price and aesthetics, some practitioners and patients will use ceramic brackets on the upper dental arch and metal brackets on the lower dental arch, as the upper arch is more prominent when a patient smiles.

Attempts to mix ceramic and metal brackets on the same arch can result in unintended buccal-lingual movement of the tooth to which the replacement bracket is attached. This is because metal brackets and ceramic brackets are provided with different slot floor thicknesses. Conventional ceramic brackets include thicker slot floor thicknesses to satisfy strength requirements.

BRIEF SUMMARY OF THE INVENTION

The present invention is directed to coordinated metal and ceramic orthodontic bracket systems that allow a practitioner to insert one or more ceramic brackets into a metal bracket system, replacing selected metal brackets with ceramic brackets, and vice-versa. In other words, a ceramic bracket system and a metal bracket system are provided, in which corresponding brackets of each system include substantially identical slot floor thicknesses so that corresponding brackets are interchangeable with each other.

The metal bracket system comprises a plurality of orthodontic brackets formed of metal. Each metal bracket is configured for placement onto a selected tooth of a dental arch. Each metal bracket includes a metal bracket bonding pad, a metal bracket body extending labially away from the bonding pad, and an arch wire slot formed within the metal bracket body. Each metal bracket includes a buccal-lingual slot floor cross-sectional thickness defined from an outer surface of the metal bracket bonding pad (against which the tooth is located) to a lingual floor of the arch wire slot. This slot floor cross-sectional thickness is commonly referred to within the industry as the "in-out" dimension.

The corresponding ceramic bracket system comprises a plurality of brackets formed from ceramic. Each ceramic bracket similarly includes a ceramic bracket bonding pad, a ceramic bracket body, and an arch wire slot. The ceramic brackets likewise include a buccal-lingual slot floor cross-sectional thickness. For any given tooth position, the corresponding metal and ceramic brackets will have substantially equal buccal-lingual slot floor cross-sectional thicknesses. Because the slot floor thicknesses are coordinated from the ceramic system to the metal system, a practitioner is able to choose whichever brackets he or she desires, using both metal and ceramic brackets on the same dental arch. Because the slot floor thicknesses are coordinated, no unintended tooth movements occur and no special bending of the arch wire to prevent such movement is required. For example, a practitioner may choose to install ceramic brackets on the incisors and canines (which are more readily visible), and metal brackets on the bicuspids and optionally on the molars.

Previous attempts to mix ceramic and metal brackets on the same arch have met with difficulties, as existing metal and ceramic bracket systems are not compatible with one another. Existing ceramic brackets are formed with significantly greater slot floor thicknesses (i.e., the distance between the bonding surface of the bonding pad and the lingual surface of the slot floor) in order to provide strength and prevent unintentional cracking of the bracket. As such, any such ad-hoc attempt to mix ceramic and metal brackets on a single dental arch would result in unintended movement of the teeth either lingually or bucally. Such undesired tooth movement would be expected to result in longer treatment times, as such movements must be corrected.

The inventors have surprisingly found that the "in-out" dimension of ceramic brackets can actually be reduced so as to be equal to the "in-out" dimension of the metal brackets, while still exhibiting sufficient strength and durability, when the ceramic brackets are machined from a bulk ceramic material. Machining rather than molding the "in-out" dimension of ceramic brackets somehow preserves bracket strength. As such, the systems do not simply adopt the greater thickness of the ceramic brackets and alter the metal brackets to include this greater "in-out" dimension. Such an overall system would be undesirable, as the metal brackets would then be very "high profile", making it difficult or impossible to bond them to closely crowded teeth. Rather, the system provides both low profile metal brackets and low profile ceramic brackets, in which corresponding brackets from each system are interchangeable with one another. As a result, the invention provides an overall bracket system that allows mixing of metal brackets and ceramic brackets for use on the same dental arch at the same time. For example, ceramic brackets are selected for the incisors and canines to provide better aesthetics through lower visibility, while metal brackets are provided for the bicuspids and molars for overall reduced price.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 1A is a cross-sectional view through a typical ceramic bracket on a lower incisor;

FIG. 1B is a transverse cross-sectional view through the ceramic bracket and tooth of FIG. 1A;

FIG. 2A is a cross-sectional view through a typical metal bracket on the same lower incisor as in FIG. 1A;

FIG. 2B is a transverse cross-sectional view through the metal bracket and tooth of FIG. 2A;

FIG. 3A is a cross-sectional view of an exemplary system of ceramic orthodontic brackets;

FIG. 3B is a cross-sectional view of an exemplary system of metal orthodontic brackets, in which the corresponding brackets of FIGS. 3A and 3B include substantially identical slot floor thickness dimensions;

DETAILED DESCRIPTION OF THE PREFERRED EMBODIMENTS

I. Introduction

Figure 4A:
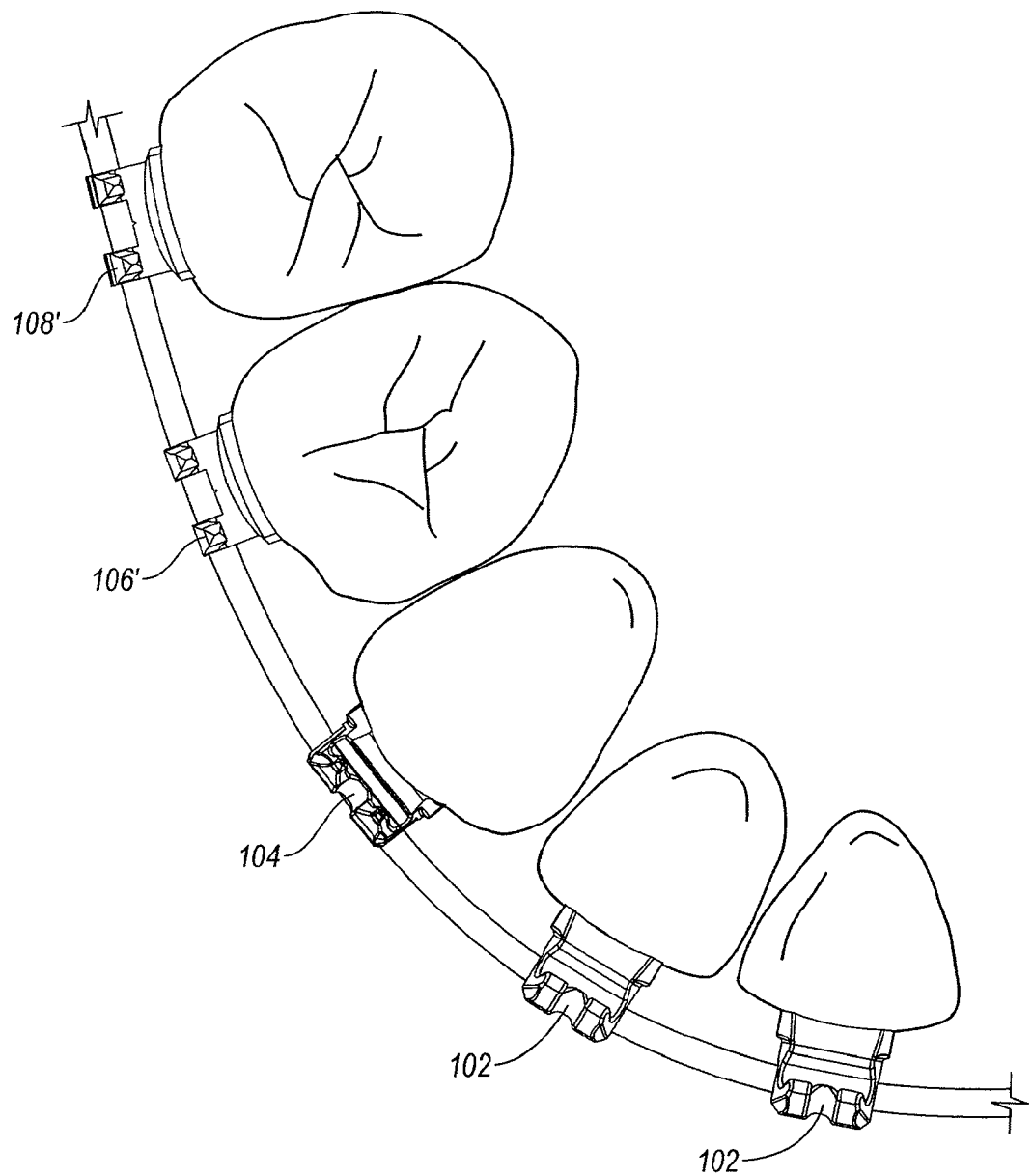
FIG. 4A an occlusal view of a the left half of a lower dental arch employing the coordinated ceramic and metal bracket systems, in which ceramic brackets are bonded to the front three teeth, and metal brackets bonded to the adjacent bicuspids.

The present invention is directed to coordinated metal and ceramic orthodontic bracket systems that allow a practitioner to insert one or more ceramic brackets into a metal bracket system, replacing selected metal brackets with ceramic brackets, and vice-versa. In other words, both a ceramic bracket system and a metal bracket system are provided, in which corresponding brackets of each system include substantially identical slot floor cross-sectional thicknesses so that corresponding brackets are interchangeable with each other.

II. Exemplary Orthodontic Bracket Systems

FIGS. 1A-1B illustrate cross-sections through a typical ceramic bracket and a typical metal bracket (FIG. 2A-2B) configured for placement on the same tooth (e.g., a lower incisor 12). As seen in FIGS. 1A-1B, the ceramic bracket 10 includes a slot floor cross sectional thickness (i.e., the "in-out" dimension) designated $T_C$. This dimension corresponds to the distance between the tooth surface and the floor of the arch wire slot. The same tooth is seen in FIGS. 2A-2B, but with a typical metal bracket 10' attached to the tooth rather than the ceramic bracket 10. The metal bracket 10' includes a slot floor cross-sectional thickness designated $T_M$. As seen, the thickness $T_C$ is significantly greater than $T_M$. According to standard practice, the "in-out" dimension is defined as the cross-sectional thickness as measured along a line bisecting the arch wire slot in an occlusal-gingival direction, as perhaps best seen in FIGS. 1B and 2B. Ceramic bracket 10 is provided with the greater "in-out" dimension $T_C$ as a result of overall strength requirements of existing ceramic brackets (which are typically formed by injection molding). It is noted that such strength requirements prevent ceramic bracket 10 from being as low of profile bracket as metal bracket 10'.

Such differences in the "in-out" slot floor thickness dimension result in an inability to replace metal bracket 10' with ceramic bracket 10 in an otherwise all metal bracket system, because the difference in the "in-out" dimensions between the brackets will result in a buccal-lingual misalignment of the tooth as treatment progresses. In other words, because the ceramic bracket inserted into the otherwise metal bracket system includes a significantly greater "in-out" dimension, correct movement of the tooth to which the ceramic bracket is attached will be disrupted. If a practitioner were to perform such an insertion of one or more ceramic brackets into a metal bracket system (e.g., because the ceramic brackets are less visible and more aesthetically pleasing), either additional compensating bends of the arch wire would be required, or treatment time will be lengthened, as the practitioner must move the teeth that now include ceramic brackets buccally-lingually to corrected locations at a later stage of treatment. Either scenario is undesirable—the formation of additional bends in the arch wire depends on the skill of the individual practitioner, and both later movement and the formation of a compensating bend require additional time.

FIGS. 3A and 3B illustrate exemplary ceramic and metal orthodontic bracket systems respectively, that are coordinated with one another so as to allow the practitioner to interchange one or more brackets from the ceramic system into the metal system or vice versa. FIG. 3A illustrates cross-sectional views of four exemplary ceramic brackets that are included in an exemplary ceramic bracket system 100. Ceramic system 100 includes a lower incisor bracket 102 (e.g., configured for placement on the central and lateral lower incisors), a lower canine bracket 104, a lower first bicuspid bracket 106, and a lower second bicuspid bracket 108. FIG. 3B illustrates an exemplary metal ceramic bracket system 100' that is also includes a lower incisor bracket 102' configured for placement on the central and lateral lower incisors, a lower canine bracket 104', a lower first bicuspid bracket 106', and a lower second bicuspid bracket 108'. As illustrated, metal bracket system 100' may include an equal number of brackets as ceramic bracket system 100. In the illustrated example, each ceramic bracket includes a metal insert 107. Such an insert is optional, but preferable, as it prevents notching of a relatively soft Ni—Ti arch wire by the harder ceramic material. Both metal and ceramic brackets further include a bonding pad 103, and a body 105 including tie wings 109.

Although corresponding brackets from each system may differ in overall shape, the "in-out" dimension $T_{1-2}$ defining the slot floor thickness of corresponding brackets 102 and 102' is substantially identical. Similarly, the "in-out" dimension of corresponding brackets 104 and 104' is substantially equal to $T_3$, the "in-out" dimension of corresponding brackets 106 and 106' is substantially equal to $T_4$, and the "in-out" dimension of corresponding brackets 108 and 108' is substantially equal to $T_5$. Providing identical "in-out" dimensions from one corresponding bracket to the next allows the practitioner to mix brackets from the different systems 100 and 100', without any risk of creating a buccal-lingual misalignment of the tooth to which the replacement bracket is attached as a result.

Figure 4B:
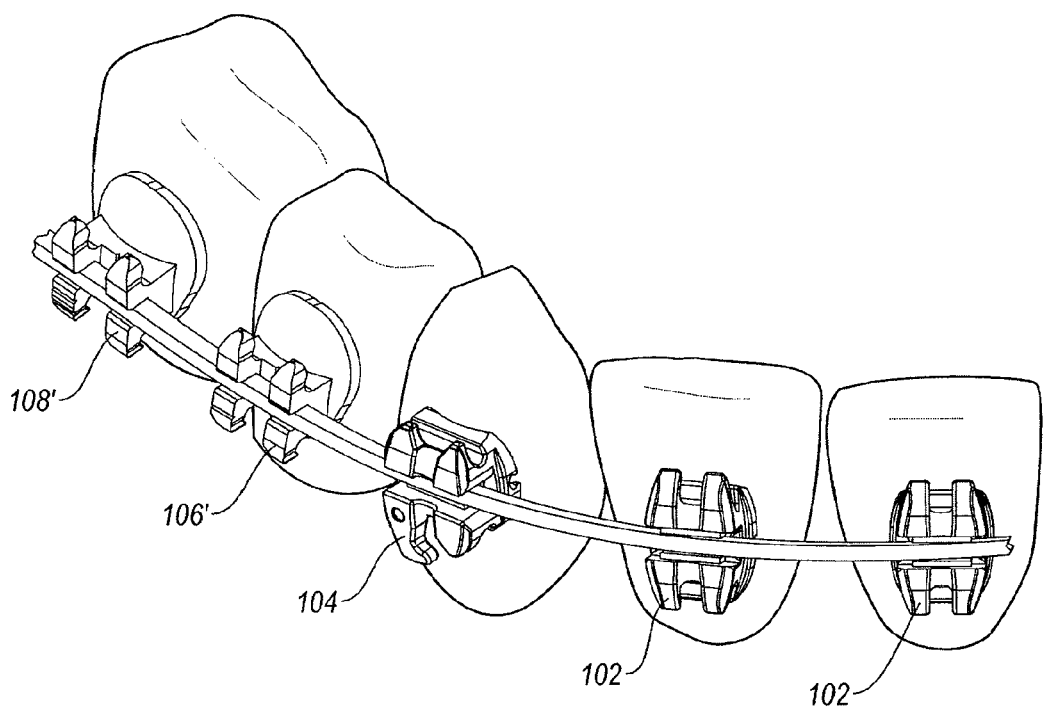
FIG. 4B is a front perspective view of the dental arch and brackets of FIG. 4A.

FIGS. 4A-4B illustrate an example in which ceramic brackets 102 have been attached to the central and lateral lower incisors. Canine ceramic bracket 104 is also attached to the canine. Metal brackets 106' and 108' have been attached to the first and second bicuspids, respectively. Because the "in-out" dimension of each corresponding bracket of systems 100 and 100' are substantially identical, there will be no need for a compensating bend or later treatment to correct an unintended buccal-lingual movement of any tooth.

Although it may be possible to form such brackets by injection molding a metal or ceramic powder along with a binder, the brackets are preferably formed by machining a bulk metal or ceramic material, as this has been found by the inventors to surprisingly allow manufacture of low profile ceramic brackets having sufficient strength. The arch wire slot or holes may be machined through the use of drill bits and/or end mills as described in U.S. Patent Application No. 61/159,859 filed Mar. 13, 2009 and entitled METHODS OF MANUFACTURING ORTHODONTIC BRACKETS INCLUDING A RECTANGULAR ARCH WIRE HOLE, herein incorporated by reference. The other bracket structures (e.g., tie wings, optional hooks, etc.), may be machined with end mills and/or other suitable tools. Such tools preferably include a carbide coating (e.g., titanium carbide and/or tungsten carbide).

Manufacture by machining allows for significantly improved dimensional tolerances, as well as significantly greater strength in the finished article. For example, machining the brackets rather than injection molding allows for use of stronger, more dense metal materials, which materials are not suitable for use in metal injection molding. Use of stronger, more dense metal materials (e.g., 17-4 and/or 17-7 class stainless steels) provides for a stronger, more dense finished product. In addition, 17-4 and 17-7 class stainless steels may be heat treated after machining to further increase strength. Such heat treatments are not possible using classes of stainless steels suitable for use in metal injection molding. By contrast, metal injection molded brackets are formed from stainless steel powder materials (e.g., 303, 304, and/or 316L class stainless steels) which, although better suited for powderization and sintering, exhibit less strength and lower density compared to 17-4 and 17-7 class stainless steel.

In addition, the strength and density of actual finished metal or ceramic brackets formed by injection molding are less than the bulk strength and density of metal or ceramic materials employed as micro air pockets can form during molding and sintering, and the strength of the finished article is reduced as the sintering process may result in weak bonding of the metal or ceramic powder. Because the brackets are machined, it is possible to form the ceramic brackets having slot floor thicknesses that are as thin as the corresponding metal bracket of the corresponding metal bracket system, while still providing sufficient strength to the ceramic bracket. This advantageously allows manufacture of coordinated metal and ceramic bracket systems in which the brackets of each system are low profile (i.e., small "in-out" dimensions) and small, which characteristic is very desirable both to the patient and practitioner. Issues of shrinkage, lack of tight tolerances, and strength reduction are minimized or eliminated when machining the brackets from a bulk metal or ceramic material. Exemplary ceramic materials include, but are not limited to, polycrystalline alumina ($Al_2O_3$), zirconia, or even monocrystalline alumina. Monocrystalline alumina is less preferred because of its brittle characteristics. Transparent or translucent polycrystalline alumina is most preferred.

According to one example, both the metal and ceramic brackets of the coordinated systems are machined so as to have about the following "in-out" dimensions:

| Tooth | "In-Out" (mm) |
|---|---|
| Upper Central Incisor | 1.041 |
| Upper Lateral Incisor | 1.219 |
| Upper Canine | 0.533 |
| Upper First Bicuspid | 0.737 |
| Upper Second Bicuspid | 0.737 |
| Lower Incisors | 1.524 |
| Lower Canine | 0.508 |
| Lower First Bicuspid | 0.762 |
| Lower Second Bicuspid | 0.864 |

It is noted that the values presented in the table are only exemplary. For example, each value may more generally range within the given value plus or minus about 10%, more preferably plus or minus about 55%, and most preferably plus or minus about 1%. The given values are preferred as they have been found to provide sufficient strength in a machined ceramic bracket, while also minimizing the buccal-lingual profile of the brackets (i.e., providing a low-profile bracket).

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A coordinated metal and ceramic orthodontic bracket system configured for interchangeable placement of individual orthodontic brackets into a bracket system for placement on a single dental arch, comprising:
   a ceramic orthodontic bracket system comprising a plurality of orthodontic bracket bodies formed of ceramic, each ceramic orthodontic bracket being configured for placement on a selected tooth of a dental arch, each ceramic orthodontic bracket including:
      a ceramic bracket bonding pad;
      a ceramic bracket body fixedly attached to and extending labially away from the bonding pad; and
      an arch wire slot formed within the ceramic bracket body;
      wherein the ceramic orthodontic bracket has a buccal-lingual slot floor cross-sectional thickness defined from a tooth attachment surface of the ceramic bracket bonding pad to a lingual floor of the arch wire slot; and
   a metal orthodontic bracket system comprising a plurality of orthodontic brackets formed of metal, each metal orthodontic bracket being configured for placement on a selected tooth of the dental arch, each metal orthodontic bracket including:
      a metal bracket bonding pad;
      a metal bracket body fixedly attached to and extending labially from the metal bracket bonding pad; and
      an arch wire slot formed within the metal bracket body;
      wherein a buccal-lingual slot floor cross-sectional thickness of each metal orthodontic bracket defined from a tooth attachment surface of the metal bracket bonding pad to a lingual floor of the arch wire slot is substantially equal to the buccal-lingual slot floor cross-sectional thickness of a corresponding ceramic orthodontic bracket configured for placement on a same tooth as the corresponding metal orthodontic bracket so that an entire ceramic orthodontic bracket is interchangeable with an entire corresponding metal orthodontic bracket.

2. A coordinated metal and ceramic orthodontic bracket system as recited in claim 1, wherein the ceramic orthodontic bracket system includes ceramic orthodontic brackets configured for placement on the incisors and canines.

3. A coordinated metal and ceramic orthodontic bracket system as recited in claim 1, wherein the metal bracket system includes metal orthodontic brackets configured for placement on the first and second bicuspids.

4. A coordinated metal and ceramic orthodontic bracket system as recited in claim 1, wherein the ceramic orthodontic brackets are machined.

5. A coordinated metal and ceramic orthodontic bracket system as recited in claim 4, wherein the ceramic orthodontic brackets comprise a material selected from the group consisting of polycrystalline alumina, monocrystalline alumina, and zirconia.

6. A coordinated metal and ceramic orthodontic bracket system as recited in claim 4, wherein the ceramic orthodontic brackets comprise translucent or transparent polycrystalline alumina.

7. A coordinated metal and ceramic orthodontic bracket system as recited in claim 1, wherein the metal orthodontic brackets are machined.

8. A coordinated metal and ceramic orthodontic bracket system as recited in claim 4, wherein the metal orthodontic brackets comprise a material selected from the group consisting of 17-4 stainless steel and 17-7 class stainless steel.

9. A coordinated metal and ceramic orthodontic bracket system as recited in claim 1, wherein the metal orthodontic bracket system and ceramic orthodontic bracket system include corresponding orthodontic brackets configured for placement on an upper central incisor, the buccal-lingual slot floor cross-sectional thickness of both corresponding orthodontic brackets being about 1.041 mm ±10 percent.

10. A coordinated metal and ceramic orthodontic bracket system as recited in claim 1, wherein the metal orthodontic bracket system and ceramic orthodontic bracket system include corresponding orthodontic brackets configured for placement on an upper lateral incisor, the buccal-lingual slot floor cross-sectional thickness of both corresponding orthodontic brackets being about 1.219 mm ±10 percent.

11. A coordinated metal and ceramic orthodontic bracket system as recited in claim 1, wherein the metal orthodontic bracket system and ceramic orthodontic bracket system include corresponding orthodontic brackets configured for placement on an upper canine, the buccal-lingual slot floor cross-sectional thickness of both corresponding orthodontic brackets being about 0.533 mm ±10 percent.

12. A coordinated metal and ceramic orthodontic bracket system as recited in claim 1, wherein the metal orthodontic bracket system and ceramic orthodontic bracket system include corresponding orthodontic brackets configured for placement on an upper first bicuspid, the buccal-lingual slot floor cross-sectional thickness of both corresponding orthodontic brackets being about 0.737 mm ±10 percent.

13. A coordinated metal and ceramic orthodontic bracket system as recited in claim 1, wherein the metal orthodontic bracket system and ceramic orthodontic bracket system include corresponding orthodontic brackets configured for placement on an upper second bicuspid, the buccal-lingual slot floor cross-sectional thickness of both corresponding orthodontic brackets being about 0.737 mm ±10 percent.

14. A coordinated metal and ceramic orthodontic bracket system as recited in claim 1, wherein the metal orthodontic bracket system and ceramic orthodontic bracket system include corresponding orthodontic brackets configured for placement on a lower incisor, the buccal-lingual slot floor cross-sectional thickness of both corresponding orthodontic brackets being about 1.524 mm ±10 percent.

15. A coordinated metal and ceramic orthodontic bracket system as recited in claim 1, wherein the metal orthodontic bracket system and ceramic orthodontic bracket system include corresponding orthodontic brackets configured for placement on a lower canine, the buccal-lingual slot floor cross-sectional thickness of both corresponding orthodontic brackets being about 0.508 mm ±10 percent.

16. A coordinated metal and ceramic orthodontic bracket system as recited in claim 1, wherein the metal orthodontic bracket system and ceramic orthodontic bracket system include corresponding orthodontic brackets configured for placement on a lower first bicuspid, the buccal-lingual slot floor cross-sectional thickness of both corresponding orthodontic brackets being about 0.762 mm ±10 percent.

17. A coordinated metal and ceramic orthodontic bracket system as recited in claim 1, wherein the metal orthodontic bracket system and ceramic orthodontic bracket system include corresponding orthodontic brackets configured for placement on a lower second bicuspid, the buccal-lingual slot floor cross-sectional thickness of both corresponding orthodontic brackets being about 0.864 mm ±10 percent.

18. A coordinated metal and ceramic orthodontic bracket system configured for interchangeable placement of individual orthodontic brackets into a bracket system for placement on a single dental arch, comprising:
a ceramic orthodontic bracket system comprising a plurality of orthodontic brackets formed of ceramic, each ceramic orthodontic bracket being configured for placement on a selected tooth of a dental arch, including ceramic orthodontic brackets configured for placement on the incisors and canines, each ceramic orthodontic bracket including:
a ceramic bracket bonding pad;
a ceramic bracket body fixedly attached to and extending labially away from the bonding pad; and
an arch wire slot formed within the ceramic bracket body;
wherein the ceramic orthodontic bracket has a buccal-lingual slot floor cross-sectional thickness defined from a tooth attachment surface of the ceramic orthodontic bracket bonding pad to a lingual floor of the arch wire slot; and
a metal orthodontic bracket system comprising a plurality of orthodontic brackets formed of metal, including metal orthodontic brackets configured for placement on the first and second bicuspids, each metal orthodontic bracket being configured for placement on a selected tooth of the dental arch, each metal orthodontic bracket including:
a metal bracket bonding pad;
a metal bracket body fixedly attached to and extending labially from the metal bracket bonding pad; and
an arch wire slot formed within the metal bracket body;
wherein a buccal-lingual slot floor cross-sectional thickness of each metal orthodontic bracket defined from a tooth attachment surface of the metal bracket bonding pad to a lingual floor of the arch wire slot is substantially equal to the buccal-lingual slot floor cross-sectional thickness of a corresponding ceramic orthodontic bracket configured for placement on a same tooth as the corresponding metal orthodontic bracket so that an entire ceramic orthodontic bracket is interchangeable with an entire corresponding metal orthodontic bracket.

* * * * *

UNITED STATES PATENT AND TRADEMARK OFFICE
CERTIFICATE OF CORRECTION

| | | |
|---|---|---|
| PATENT NO. | : 8,882,498 B2 | Page 1 of 1 |
| APPLICATION NO. | : 13/255489 | |
| DATED | : November 11, 2014 | |
| INVENTOR(S) | : Lewis et al. | |

It is certified that error appears in the above-identified patent and that said Letters Patent is hereby corrected as shown below:

In the Specification

<u>Column 3</u>
Line 37, change "of a the left" to --of the left--

Signed and Sealed this
First Day of December, 2015

Michelle K. Lee
*Director of the United States Patent and Trademark Office*